United States Patent [19]

Wun et al.

[11] Patent Number: 4,966,852

[45] Date of Patent: Oct. 30, 1990

[54] DNA CLONE OF HUMAN TISSUE FACTOR INHIBITOR

[75] Inventors: Tze-Chein Wun, St. Louis; Kuniko K. Kretzmer, Eureka; George J. Broze, Jr., St. Louis, all of Mo.

[73] Assignees: Monsanto Company; Washington University, both of St. Louis, Mo.

[21] Appl. No.: 123,753

[22] Filed: Nov. 23, 1987

Related U.S. Application Data

[63] Continuation-in-part of Ser. No. 77,366, Jul. 23, 1987.

[51] Int. Cl.$^5$ .................... C12N 7/00; C12N 9/00; C12N 15/12
[52] U.S. Cl. .................... 435/235; 536/27; 435/69.1; 435/69.2; 435/183; 435/320; 935/31
[58] Field of Search .................... 530/350; 536/27; 435/68, 172.3, 69.1, 317.1, 212, 235, 212, 183, 69.2, 320; 935/31

[56] References Cited

U.S. PATENT DOCUMENTS

| | | | |
|---|---|---|---|
| 4,393,133 | 7/1983 | Knowles et al. | 435/6 |
| 4,495,280 | 1/1985 | Bujard | 435/6 |
| 4,788,135 | 11/1988 | Davis | 435/6 |

OTHER PUBLICATIONS

Warn-Cramer B. et al., Nov. 19, 1986, "Partial Purification of a Faehr x Dependent Phama Inhibitor of the Factor VIIa/Tissue Factor Complex", American Heart Assn. Program lecture, Dallas Tex.
Lackwer K. J. et al, 1985, Nucl. Acids Res 13(12) 4597–4608.
Carson S. D., Jan. 15, 1987, J. Bl. 262(2) 718–721.
Kaumeyer J. F. et al., 1986, Nucleic Acids Res 14(20) 7839–7850.
Hochstrasser K and Wachter E, 1983, Hoppe-Seyler S. Z. Physiol. Chem. 364:1679–1687.
Broze G. J. et al, 1986, Characterization of the Inhibition of Tissue Factor in Serum, Amer. Heart Assn. Abstracts, Nov. 19, 1986.
Bourguignon et al., 1985, Biochem. Biophys. Res. Comm. 131(3) 1146–53.
Salier J P et al, 1987, Proc Natl Acad Sci, 84:8277–8276.
Warn–Cramer B J et al, 1987, Thrombosis Research, 48:11–22.
Kikulani M et al, 1986, Cell 47:657–665.
Broze and Miletich, Blood 69, 150–155 (1987).
Broze and Miletich, Proc. Natl. Acad. Sci. USA 84, 1886–1890 (1987).
Sanders et al., Blood 66, 204–212 (1985).

*Primary Examiner*—Robin L. Teskin
*Assistant Examiner*—Michelle S. Marks
*Attorney, Agent, or Firm*—Scott J. Meyer; James W. Williams, Jr.

[57] ABSTRACT

A cDNA clone having a base sequence for human tissue factor inhibitor (TFI) has been developed and characterized and the amino acid sequence of the TFI has been determined.

3 Claims, 6 Drawing Sheets

```
  1         GGC GGG TCT GCT TCT AAA AGA AGA AGT AGA GAA GAT AAA TCC TGT CTT CAA TAC CTG GAA GGA AAA ACA AAA CCT CAA CTC CGT TTT    16

91  GAA AAA AAC ATT CCA AGA ACT TTC ATC AGA GAT TTT ACT TAG ATG ATT TAC ACA ATG AAG AAA GTA CAT CAT GCA CTT TGG GCT TCT GTA TGC    46
     Glu Lys Asn Ile Pro Arg Thr Phe Ile Arg Asp Phe Thr         Met Ile Tyr Thr Met Lys Lys Val His His Ala Leu Trp Ala Ser Val Cys
                                                             +1

181  CTG CTG CTT AAT CTT GCC CCT GCC CCT AAT CTT GAT GAT TCT GAG GAA GAT GAA CAC ACA ATT ATC ACA GAT ACG GAG TTG CCA CCA    76
     Leu leu Leu Asn Leu Ala Pro Ala Pro Asn Leu Asp Asp Ser Glu Glu Asp Glu His Thr Ile Ile Thr Asp Thr Glu Leu Pro Pro 271  CTG AAA CTT ATG CAT TCA TTT GCA TTC AAG GCG GAT GAT GGC CCA TGT AAA GCA ATC ATG AAA AGA TTT TTC AAT ATT TTC ACT    106
     Leu Lys Leu Met His Ser Phe Ala Phe Lys Ala Asp Asp Gly Pro Cys Lys Ala Ile Met Lys Arg Phe Phe Asn Ile Phe Tyr 361  CGA CAG TGC GAA GAA TTT ATA TAT GGG GGA TTC GTA TTT GAA AGT CTG GAA GAG TGC AAA AAA ATG TGT ACA AGA    136
     Arg Gln Cys Glu Glu Phe Ile Tyr Gly Gly Phe Val Phe Glu Ser Leu Glu Glu Cys Lys Lys Met Cys Thr Arg 451  GAT AAT GCA AAC AGG ATT ATA AAG ACA ACA TTG CAA CAA AAG CCA GAT TTC TGC TTT GAA GAA GAT CCT GGA ATA TGT CGA GGT    166
     Asp Asn Ala Asn Arg Ile Ile Lys Thr Thr Leu Gln Gln Lys Pro Asp Phe Cys Phe Glu Glu Asp Pro Gly Ile Cys Arg Gly 541  TAT ATT ACC AGG TAT TTT TAT AAC AAT CAG ACA CGT GAA CGT TTC AAG TTC TAT GGT GGA TTC GGC AAT ATG AAC AAT TTT GAG    196
     Tyr Ile Thr Arg Tyr Phe Tyr Asn Asn Gln Thr Arg Glu Arg Phe Lys Phe Tyr Gly Gly Phe Gly Asn Met Asn Phe Glu 631  ACA CTG GAA GAA TGC AAG AAC ATT TGT GAA GAT GGT TTC CAG GTG GAT CTG AAT GGT TAT GGA ACC CAG CTC AAT GCT GTG AAT GCT AAC    226
     Thr Leu Glu Glu Cys Lys Asn Ile Cys Glu Asp Gly Phe Gln Val Asp Leu Asn Gly Tyr Gly Thr Gln Leu Asn Ala Val Asn 721  TCC CTG ACT CCC CAA TCA ACC AAG GTT CCC AGC CTT TTT CAC TGG CCT TCA ACT CCA GCA GAC AGA GGA TTG TGT    256
     Ser Leu Thr Pro Gln Ser Thr Lys Val Pro Ser Leu Phe His Trp Pro Ser Leu Thr Pro Ala Asp Arg Gly Leu Cys 811  CGT GCC AAT GAG AAC AGA TTC TAC TAC AAT TCA ATT GGG AAA TGC CGC CCA TTT AAG TAC AGT GGA TGT GGG AAT GAA AAT
     Arg Ala Asn Glu Asn Arg Phe Tyr Tyr Asn Ser Val Ile Gly Lys Cys Arg Pro Phe Lys Tyr Ser Gly Cys Gly Asn Glu Asn
```

FIG. 3

```
901  TTT ACT TCC AAA CAA GAA TGT CTG AGG GCA TGT AAA AAA GGT TTC ATC CAA AGA ATA TCA AAA GGA GGC CTA ATT AAA ACC AAA AGA AAA
     Phe Thr Ser Lys Gln Glu Cys Leu Arg Ala Cys Lys Lys Gly Phe Ile Gln Arg Ile Ser Lys Gly Gly Leu Ile Lys Thr Lys Arg Lys  286

991  AGA AAG CAG AGA GTG AAA ATA GCA TAT GAA GAA ATT TTT GTT AAA AAT ATG TGA ATT TGT TAT AGC AAT GTA ACA TTA ATT CTA CTA
     Arg Lys Gln Arg Val Lys Ile Ala Tyr Glu Glu Ile Phe Val Lys Asn Met End                                              304

1081 AAT ATT TTA TAT GAA ATG TTT CAC TAT GAT TTT CTA TTT TTC TTC TAA AAT CGT TTT AAT TAA TAT GTT CAT TAA ATT TTC TAT GCT TAT

1171 TGT ACT TGT TAT CAA CAC GTT TGT ATC AGA GTT GCT TTT CTA ATC TTG TTA TTC TAG GTC TGT AAT TTA TTA ACT GGC TAC

1261 TGG GAA ATT ACT TAT TTT CTG GAT CTA TCT GTA TTT TCA TTT AAC TAC AAA TTA TCA TAC TAC CGG CTA CAT CAA ATC AGT CCT TTG ATT

1351 CCA TTT GGT GAC CAT CTG TTT GAG AAT ATG ATC ATG TAA ATG ATT ATC TCC TTT ATA GCC TGT AAC CAG ATT AAG CCC CCC
```

```
          1                                                              50
 1   PSLFNRDPPI PAAQRPDFCL EPPYTGPCKA RIIRYFYNAK AGLCQTFVYG GCRAKRNNFK SAEDCMRTCG GAIGPWGKTG GRAEGEGKG
 2              FQTPPDLCQ LPQARGPCKA ALLRYFYBST SNACEPFTYG GCQQNBNFE  TTEMCLRICE PPQQTDKS
 3              TERPDFCL  EPPYTGPCKA AMIRYFYNAK AGFCETFVYG GCRAKSNNFK SAEDCMRTCG GA
 4              QGRPSFCN  LPAETGPCKA SFRQYYYNSK AGFCETFVYG GCRGNQQNRFD TTQQCQGVCV
 5              QGDKRDICR LPPEQGPCKG RIPRFYNPA  SRMCESFIYG GCKGNKNNFK TKAECVRACR PPERPGVCPK TSGPGICLHG
 6              QDHPKFCY  LPADPGRCKA HIPRFYYDSA SMKCNKFIYG GCPGNANMFK TMDECRQTCG ASA
 7              RPDFCE    LPAETGLCKA YIRSFHYNLA AQQCLQFIYG GCGGNANRFK TIDECRRTCV G
 8              RPRFCE    LPAETGLCKA RIRSFHYNRA AQQCLEFIYG GCGGNANRFK TIDECHRTCV G
 9              HDRPTFCN  LAPESGRCRG HLRRIYYNLE SNKCKFIYG  GCGGNANNFE TRDECRETCG GK
10              RDRPKFCY  LPADPGRCLA YMPRFYYNPA SNKCEKFIYG GCRGNANNFE TMDECRHTCV ASGIQPR
11              QPRRKLCI  LHRNPGRCYD KIPAFYYNQK KKQCERFDWS GCGGNSNRFK TIEECRRTCI G
12              RPYACE    LIVAAGPCMF FISAFYYSKG ANKCYPFTYS GCRGNANRFK TIEECRRTCV V
13              LQHRTFCK  LPAEPGPCKA SIPAFYYNWA AKKCCQLFHYG GCKGNANRFS TIEKCRHACV G
14              QPLRKLCI  LHRNPGRCYQ KIPAFYYNQK KKQCZGFTWS GCGGNSNRFK TIEECRRTCI RK
15              AAKYCK    LPLRIGPCKR KIPSFYYKWK AKQCLPFDYS GCGGNANRFK TIEECRRTCV G
16              RQRHRDCD  KPPDKGNC.G PVRAFYYDTR LKTCKAFQYR GCDDHGNFK  SDHLCRCECE LY
17              RQRHRDCD  KPPDKGNC.G PVRAFYYDTR LKTCKAFQYR GCDDHGNFK  TETLCRCECL VYP
18              RKRHPDCD  KPPDTKIC.Q TVRAFYYKPS AKRCVQFRYG GCDDHGNFK  SDHLCRCECE LYR
19(1)           KEDSCQ    LOHAQGPCLG MISRYFYNGT SMACETFQYG GCLGNGNNFA SQKECLQTCR T
19(2)           VAACN     LPIVQGPCRA FIRLWAFDAA QGKCVLFTYG GCRGNGNKFY SQKECKEYCG IPGDGDEELL R
20(1)           KEDSCQ    LGYSQGPCLG MIKRYFYNGS FIRLWAFDAA QGKCVLFNYG GCMGNGNNFV SQKECLQTCR T
20(2)           VSACS     LPIVQGPCRA FIRLWAFDAA QGKCVLFNYG GCQGNGNKFY SQKECKEYCG VPGEEDEELL R
21(1)           KADSCQ    LDYSQGPCLG LFKRYFYNGT SMACETFLYG GCMGNLNNFL SQKECLQTCR T
21(2)           VEACN     LPIVQGPCRA FIQLWAFDAV KGKCVRFSYG GCKGNGNNFY SQKECKEYCG IPGEADERLL R
22(1)           KEDSCQ    LGYSAGPCMG MTSRYFYNGT SMACETFQYG GCMGNGNNFY TEKECLQTCR T
22(2)           VAACN     LPIVRGPCRA FIQLWAFDAV KGKCVLFPYG GCQGNGNKFY SEKECREYCG VPGDGDEELL R
23(1)           LKLMHSFCA FKADDGPCKA IMKRFFFNIF TRQCEEFIYG GCEGNQNRFE SLEECKKMCT RDNANRIIKT TL
23(2)           QQEKPOFCF LEEDPGICRG YITRYFYNNQ TKQCERFKYG GCLGNMNNFE TLEECKNICE DGPNGFQVDN YG
23(3)           EFHGPSWCL TPADRGLCRA NENRFYYNSV IGKCRPFKYS GCGGNENNFT SKQECLRACK KGFIQRISKG GL
Consensus       ........C. ......G.C. .........  ....F..... GC........ ...C....F. ...C....C. .....C.
```

DNA CLONE OF HUMAN TISSUE FACTOR INHIBITOR

CROSS-REFERENCE TO RELATED APPLICATION

This is a continuation-in-part of copending application Ser. No. 77,366, filed July 23, 1987.

BACKGROUND OF THE INVENTION

This invention relates to a coagulation inhibitor known as tissue factor inhibitor (TFI) and alternatively as lipoprotein associated coagulation inhibitor (LACI). More particularly, the invention relates to a cDNA clone representing essentially the full size TFI.

The coagulation cascade that occurs in mammalian blood comprises two distinct systems - the so-called intrinsic and extrinsic systems. The latter system is activated by exposure of blood to tissue thromboplastin (Factor III), hereinafter referred to as tissue factor (TF). Tissue factor is a lipoprotein that arises in the plasma membrane of many cell types and in which the brain and lung are particularly rich. Upon coming into contact with TF, plasma Factor VII or its activated form, Factor VII$_a$, forms a calcium-dependent complex with TF and then proteolytically activates Factor X to Factor X$_a$, and Factor IX to Factor IX$_a$.

Early studies concerning the regulation of TF-initiated coagulation showed that incubation of TF (in crude tissue thromboplastin preparations) with serum inhibited its activity in vitro and prevented its lethal effect when it was infused into mice. Extensive studies by Hjort, *Scand. J. Clin. Lab. Invest.* 9, Suppl. 27, 76–97 (1957), confirmed and extended previous work in the area, and led to the conclusion that an inhibitory moiety in serum recognized the Factor VII-TF complex. Consistent with this hypothesis are the facts that the inhibition of TF that occurs in plasma requires the presence of Ca$^{2+}$ (which is also necessary for the binding of Factor VII/VII$_a$ to TF) and that inhibition can be prevented and/or reversed by chelation of divalent cations with EDTA. More recent investigations have shown that not only Factor VII$_a$ but also catalytically active Factor X$_a$ and an additional factor are required for the generation of TF inhibition in plasma or serum. See Broze and Miletich, *Blood* 69, 150–155 (1987), and Sanders et al., Ibid., 66, 204–212 (1985). This additional factor, defined herein as tissue factor inhibitor (TFI), and alternatively as lipoprotein associated coagulation inhibitor (LACI), is present in barium-absorbed plasma and appears to be associated with lipoproteins, since TFI functional activity segregates with the lipoprotein fraction that floats when serum is centrifuged at a density of 1.21 g/cm$^3$. According to Broze and Miletich, supra, and *Proc. Natl. Acad. Sci. USA* 84, 1886–1890 (1987), HepG2 cells (a human hepatoma cell line) secrete an inhibitory moiety with the same characteristics as the TFI present in plasma.

In copending application Ser. No. 77,366 pending filed July 23, 1987, a purified tissue factor inhibitor (TFI) is disclosed which was secreted from HepG2 cells. It was found to exist in two forms, a TFI$_1$, migrating at about 37–40,000 daltons and a TFI$_2$ at about 25–26,000 daltons, as determined by sodium dodecylsulfate polyacrylamide gel electrophoresis (SDS-PAGE). A partial N-terminal amino acid sequence for the TFI was assigned as:

$\overset{1}{X}$—X—Glu—Glu—Asp—Glu—Glu—His—Thr—Ile—Ile—Thr—Asp—Thr—$\overset{15}{Glu}$—

$\overset{16}{Leu}$—Pro—Pro—Leu—Lys—Leu—Met—His—Ser—Phe—(Phe)—$\overset{27}{Ala}$ wherein X—X had not been determined. The disclosure of said application is incorporated herein by reference.

BRIEF DESCRIPTION OF THE INVENTION

In accordance with the present invention, the complete coding sequence of a cDNA clone representing essentially the full size tissue factor inhibitor (TFI) has been developed.

Initially, human placental and fetal liver λgt11 cDNA libraries were screened with a rabbit polyclonal antiserum raised against a purified TFI. Immunologically positive clones were further screened for $^{125}$I-Factor X$_a$ binding activity. Seven clones were obtained which were immunologically and functionally active. The longest clone, placental-derived λP9, was 1.4 kilobases (kb) long while the other six were 1.0 kb in length. Partial DNA sequencing showed the 1.0 kb clones to have sequences identical to part of the longer 1.4 kb clone. Nucleotide sequence analysis showed that λP9 consisted of a 1432 basepair (bp) cDNA insert that includes a 5'-noncoding region of 133 bp, an open reading frame of 912 bp, a stop codon, and a 3'-noncoding region of 384 bp.

The cDNA sequence encodes a 31,950 Dalton protein of 276 amino acids which includes 18 cysteines and 7 methionines. The translated amino acid sequence shows that a signal peptide of about 28 amino acids precedes the mature TFI protein. It will be understood that the "mature" TFI is defined to include both TFI and methionyl TFI by virtue of the ATG translational codon in the λP9 clone described herein.

There are three potential N-linked glycosylation sites in the TFI protein with the sequence Asn-X-Ser/Thr, wherein X can be any of the common 20 amino acids. These sites are at amino acid positions Asn 145, Asn 195, and Asn 256, when the first methionine after the 5'-noncoding region is assigned amino acid position +1.

The translated amino acid sequence of TFI shows several discernible domains, including a highly negatively charged N-terminal, a highly positively charged carboxy-terminal, and an intervening portion consisting of 3 homologous domains with sequences typical of Kunitz-type enzyme inhibitors. Based on a homology study, TFI appears to be a member of the basic protease inhibitor gene superfamily.

The original source of the protein material for developing the cDNA clone λP9 was human placental tissue. Such tissue is widely available after delivery by conventional surgical procedures. The λgt11 (lac5 nin5 c1857 S100) used herein is a well-known and commonly available lambda phage expression vector. Its construction and restriction endonuclease map is described by Young and Davis, *Proc. Natl. Acad. Sci. USA* 80, 1194–1198 (1983).

Northern blot analysis showed that the following liver-derived cell lines: Chang liver, HepG2 hepatoma, and SK-HEP-1 hepatoma, all contained 2 major species of mRNA (1.4 and 4.4 kb) which hybridized with the TFI cDNA.

The cloning of the cDNA for TFI and development of its entire protein sequence and structural domains as disclosed herein permits detailed structure-functional analyses and provides a foundation for study of its biosynthetic regulations. The invention thus is important to medical science in the study of the coagulation cascade with respect to agents which are able to inhibit Factor $X_a$ and Factor $VII_a$/TF enzymatic complex.

DETAILED DESCRIPTION OF THE INVENTION

Figure 1:

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which:

FIG. 1 shows the screening of λgt11 clones with $^{125}$I-Factor $X_a$. Cloned phage lysates (0.1 ml) were spotted on a nitrocellulose paper by suction using a dot blot apparatus. The nitrocellulose paper was then probed with $^{125}$I-Factor $X_a$ and autoradiographed as described hereinafter. The clones that appear as dark spots are positive clones that bind $^{125}$I-Factor $X_a$. Control λgt11 (lower right corner) and other clones do not bind $^{125}$I-Factor $X_a$.

Figure 2:
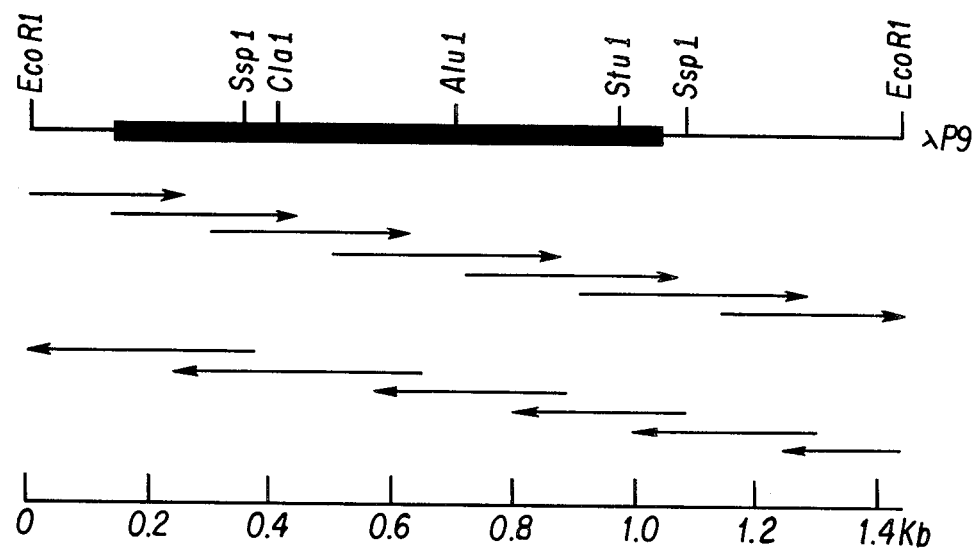

FIG. 2 shows a partial restriction map and sequencing strategy for the λP9 inserts. The scale at the bottom indicates the nucleotide position. The thick bar represents the coding region. The thin bars represent 5'- and 3'-noncoding regions. The restriction endonuclease sites were confirmed by digestion. The arrows show the overlapping M13 clones used to sequence the cDNA.

FIG. 3 shows the nucleotide sequence and translated amino acid sequence of the human TFI cDNA. Nucleotides are numbered on the left and amino acids on the right. The underlined sequences have been independently confirmed by amino acid sequence analysis of the purified TFI protein and two V$_8$ protease + trypsin digested peptides. Amino acid + 1 was assigned to the first methionine after a stop codon of the 5'-noncoding region. Potential N-lined glycosylation sites are marked by asterisks.

Figure 4:
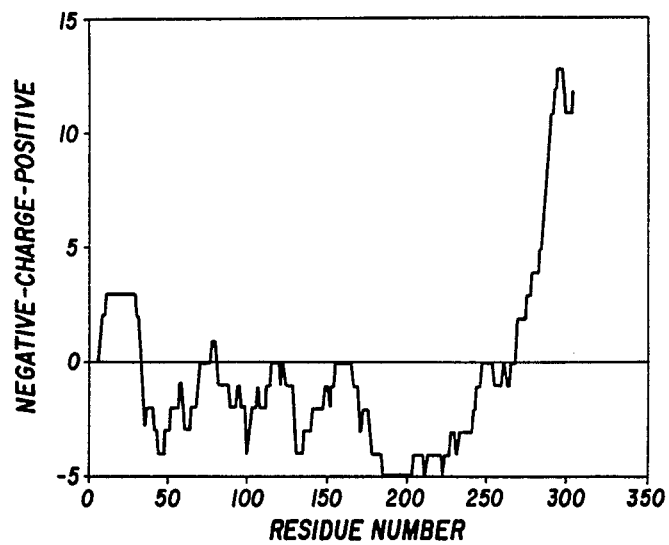

FIG. 4 is a graphical representation which shows the charge distribution of the amino acid sequence in TFI. Charges are calculated from the first residue to the i-th residues and displayed at the i-th residue. Thus the value of the i-th position is the summation of all charges from the first residue to the i-th residue and the difference of the charges between the i-th and j-th residue (j>i) is the net charge of the fragment from i-th to j-th residue.

Figure 5:
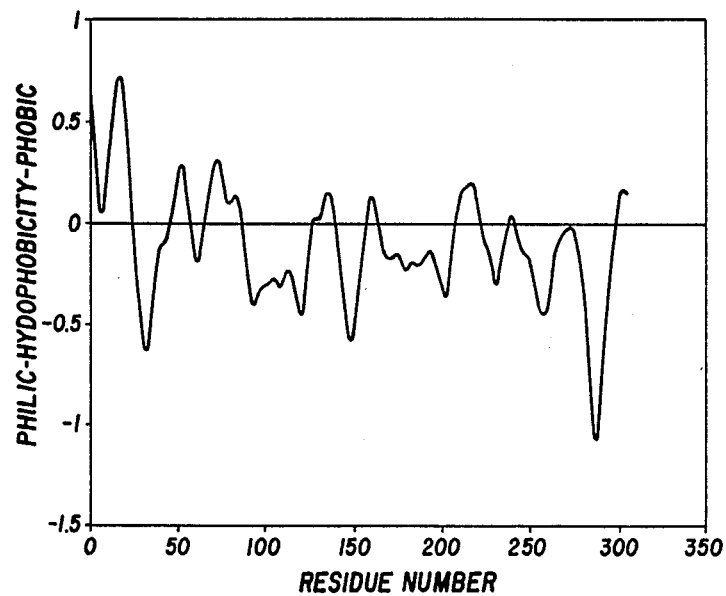

FIG. 5 is a graphical representation which shows the hydrophobicity profile of TFI. The hydrophobicity profile was analyzed by a computer program whereby the hydrophobicity index of the amino acid residues is defined as the depth to which an amino acid residue is buried inside a protein (from X-ray crystallographic data) [Kidera et al., *J. Protein Chem.* 4, 23–55 (1985)]. The hydrophobicity profile along the sequence was smoothed using the program ICSSCU in IMSL LIbrary [IMSL Library Reference Manual, 9th ed., Institute for Mathematical and Statistical Subroutine Library, Houston, Texas (1982)].

FIG. 6 shows an alignment of the basic protease inhibitor domains of TFI with other basic protease inhibitors. All the sequences except TFI were obtained from the National Biomedical Research Foundation Protein Sequence Database (Georgetown University, Washington, D.C., release 13, June 1987). 1. Bovine basic protease inhibitor precursor; 2. Bovine colostrum trypsin inhibitor; 3. Bovine serum basic protease inhibitor; 4. Edible snail isoinhibitor K; 5. Red sea turtle basic protease inhibitor (only amino acids 1–79 presented); 6. Western sand viper venom basic protease inhibitor I; 7. Ringhals venom basic protease inhibitor II; 8. Cape cobra venom basic protease inhibitor II; 9. Russell's viper venom basic protease inhibitor II; 10. Sand viper venom basic protease inhibitor III; 11. Eastern green mamba venom basic protease inhibitor I homolog; 12. Black mamba venom basic protease inhibitor B; 13. Black mamba venom basic protease inhibitor E; 14. Black mamba venom basic protease inhibitor I; 15. Black mamba venom basic protease inhibitor K; 16. β-1-Bungarotoxin B chain (minor); 17. β-1-Bungarotoxin B chain (major); 18. β-2-Bungarotoxin B chain; 19. Horse inter-α-trypsin inhibitor [amino acids 1–57(1); 58–123 (2)]; 20. Pig inter-α-trypsin inhibitor [amino acids 1–57(1); 58–123(2)]; 21. Bovine inter-α-trypsin inhibitor [amino acids 1–57(1); 58–123(2)]; 22. Human α-1-microglobulin/inter-α-trypsin inhibitor precursor [amino acids 227–283(1); 284–352(2)]; 23. TFI [amino acids 47–117(1); 118–188(2); 210–280(3)]. Gaps were included in 16, 17, 18 to achieve best alignment. Standard one letter codes for amino acids are used.

Figure 7:
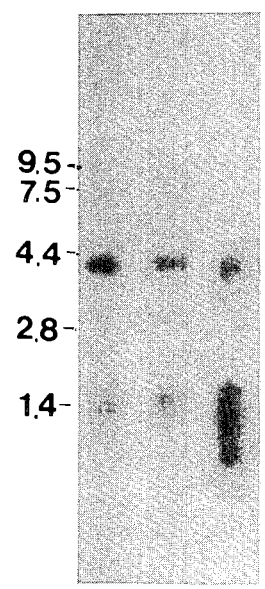

FIG. 7 shows the Northern blot analysis of RNAs from 3 liver-derived cell lines. Ten µg of poly(A)+ RNA were used per lane. Lane 1, Chang liver cell; lane 2, SK-HEP-1 hepatoma cell; lane 3, HepG2 hepatoma cell.

Standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP). As is conventional for convenience in the structural representation of a DNA nucleotide sequence, only one strand is shown in which A on one strand connotes T on its complement and G connotes C. Amino acids are shown either by three letter or one letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases described herein have the following restriction sequences and (indicated by arrows) cleavage patterns:

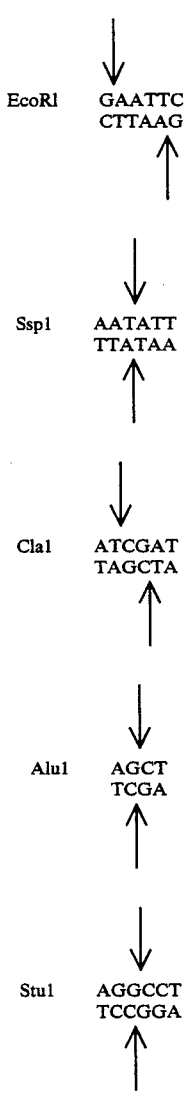

In order to illustrate specific preferred embodiments of the invention in greater detail, the following exemplary laboratory preparative work was carried out.

EXAMPLE 1

Materials

Human placental and fetal liver cDNA libraries were obtained from Clontech Laboratories, Inc. The protoblot immunoscreening kit was purchased from Promega Biotech Restriction enzymes were from New England Biolabs. Calf intestine alkaline phosphatase, T4 DNA ligase, DNA polymerase I (Klenow), exonuclease III and S1 nuclease were from Boehringer Mannheim dNTPs were from P. L. Biochemicals. 5'-[α-$^{35}$S]-thio-dATP (600 Ci/mmol) was from Amersham. Sequencing kit (Sequenase) was from United States Biochemical Corp. Chang liver cells (ATCC CCL 13) and HepG2 hepatoma cells (ATCC HB 8065) were obtained from the American Type Culture Collection. SK-HEP-1 hepatoma cells were originally derived from a liver adenocarcinoma by G. Trempe of Sloan-Kettering Institute for Cancer Research in 1971 and are now widely and readily available.

$^{125}$I-Factor $X_a$ was prepared by radiolabeling using Iodo-gen. The specific activity was 2000 dpm/ng. Greater than 97% of radioactivity was precipitable with 10% trichloroacetic acid (TCA). The iodinated protein retained >80% of their catalytic activity toward Spectrozyme $X_a$ (American Diagnostica product).

An anti-TFI-Ig Sepharose® 4B column was prepared as follows: A peptide (called TFI-peptide) containing a sequence corresponding to the amino acid sequence 3-25 of the mature TFI was synthesized using Biosystem's solid phase peptide synthesis system. The TFI-peptide (5 mg) was conjugated to 10 mg of Keyhole lympet hemocyanin by glutaraldehyde. Two New Zealand white rabbits were each immunized by intradermal injection with a homogenate containing 1 ml of Freund complete adjuvant and 1 ml of conjugate (200 μg of TFI-peptide). One month later the rabbits were each boosted with a homogenate containing 1 ml of Freund incomplete adjuvant and 1 ml of conjugate (100 μg of conjugate). Antiserum was collected each week for 3 months and booster injections were performed monthly. To isolate specific antibody against TFI-peptide, the antiserum was chromatographed on a TFI-peptide Sepharose 4B column. The column was washed with 10 volumes of PBS (0.4 M NaCl-0.1 M benzamidine-1% Triton® X-100) and the same solution without Triton X-100. The antibody was eluted with 0.1 M glycine/HCl, pH 2.2, immediately neutralized by adding 1/10 volume of 1 M Tris-OH and dialyzed against saline solution. The isolated antibody was coupled to cyanogen bromide activated Sepharose 4B by the manufacturer's (Pharmacia) method and used to isolate TFI from the cell culture medium.

Chang liver cell was cultured by the method described previously by Broze and Miletich, *Proc. Natl. Acad. Sci. USA* 84, 1886–1890 (1987). The conditioned medium was chromatographed on the anti-TFI-Ig Sepharose 4B column. The column was washed with 10 volumes of PBS-1% Triton X-100 and PBS. The bound TFI was eluted with 0.1 M glycine/HCl, pH 2.2. The immunoaffinity isolated TFI was further purified by preparative sodium dodecylsulfate polyacrylamide gel electrophoresis (Savant apparatus). Amino acid analysis of the final product showed the same amino terminal sequence as the TFI isolated from HepG2 cells as described in copending application, Ser. No. 77,366, pending filed July 23, 1987. The isolated Chang liver TFI was then used to immunize rabbits by the immunization protocol described above. The antiserum obtained had a titer of about 100 μg/ml in the double immunodiffusion test. This antiserum was used in the immuno-screening of λgtll cDNA libraries.

Methods

Isolation of cDNA clones.

Methods for screening the placental and fetal liver cDNA libraries with antibody, plaque purification, and preparation of λ-phage lysate and DNA were as described by Wun and Kretzmer, FEBS Lett. 210, 11–16 (1987). The antiserum was pre-adsorbed with BNN97 λgtll lysate and diluted 1/500 for screening the library.

Screening of factor $X_a$ binding activity

Recombinant proteins induced by isopropyl-β-thiogalactoside from immuno-positive λ-phage isolates or from control λgt11 were screened for Factor $X_a$ binding activity. The λ-phage lysates (0.1 ml) were filtered through a nitrocellulose paper using a dot-blot apparatus (Bio Rad). The nitrocellulose paper was then immersed and agitated in a phosphate buffered saline containing 5 mg/ml bovine serum albumin and 2.5 mg/ml bovine gamma globulin at room temperature for 1 h. The solution was replaced with $^{125}$I-Factor $X_a$ ($1.0 \times 10^6$ cmp/ml) dissolved in the same solution supplemented with 0.1 mg/ml heparin and the agitation continued for another hour. The nitrocellulose paper was then washed with phosphate buffered saline containing 0.05% Tween® 20. The washing buffer was changed every 5 min., 4 times. The nitrocellulose paper was then air-dryed and prepared for autoradiography using Kodak XR5 film. The film was developed after 1 week exposure.

Preparation of poly(A)+ RNA and Northern blotting. Total RNAs were prepared from cultured Chang liver cell, HepG2 hepatoma cell and SK-HEP-1 hepatoma cell using the sodium perchlorate extraction method of Lizardi, and Engelberg, *Anal. Biochem.* 98, 116–122, (1979). Poly(A)+ RNAs were isolated by batch-wise adsorption on oligo(dT)-cellulose (P-L Biochemical, type 77F) using the procedure recommended by the manufacturer. For Northern blot analysis, 10 μg each of poly(A)+ RNA was treated with glyoxal [Thomas, *Methods Enzymol.* 100, 255–266 (1983)] and subjected to agarose gel electrophoresis in a buffer containing 10 mM sodium phosphate, pH 7.0. Bethesda Research Laboratory's RNA ladder was used as a molecular weight marker. The RNAs were transblotted onto a nitrocellulose paper which was then baked at 80° for 2 h. The insert DNA of λP9 clone was radiolabeled with $^{32}$P by nick translation and used as a probe [Maniatis et al., *Molecular Cloning: A Laboratory Model,* Cold Spring Laboratory, Cold Spring Harbor, N.Y., (1982)]. The blot was hybridized with $5 \times 10^6$ cpm of the probe in 5 ml of a solution containing 50% formamide, 5X SSC, 50 mM sodium phosphate, pH 7.0, 250 μg/ml denatured salmon sperm DNA, and 1X Denhardt's solution at 42° for 16 h. The filter was washed in 0.1% sodium dodecylsulfate (SDS), 2X SSC at room temperature 3 times, each time 5 min., and in 0.1% SDS, 0.2 X SSC at 50° twice, each 5 min. The nitrocellulose paper was then air dried, autoradiographed for 3 days at −70° using Kodak XAR-5 film and intensifying screen.

Other recombinant DNA methods.

Preparation of cloned λgt11 DNA, subcloning in pUC19 plasmid and M13mp18 vector, generation of deletion by exonuclease III digestion and DNA sequencing by dideoxy method [Sanger et al., *Proc. Natl. Acad. Sci. USA* 83, 6776–6780 (1977)], were performed as described by Wun and Kretzmer, supra.

The program FASTP written by Lipman and Pearson, *Science* 227 1435–1441 (1985), was used to identify homologous families of proteins from National Biomedical Research Foundation Sequence Data Bank (release 13, June 1987) and to align the sequences within the homologous family.

RESULTS

Screening of cDNA libraries

A number of cell lines were screened for the presence of TFI in the conditioned media and it was found that several liver-derived cell lines, Chang liver, HepG2 hepatoma, and SK-HEP-1 hepatoma secrete TFI in culture. Initially, an antiserum against TFI was used to screen a human fetal liver λgt11 cDNA library ($10^6$ plaque forming units), and 15 immunologically positive clones were obtained. Subsequently, the same method was used to screen a placental λgt11 cDNA library. Out of $10^6$ plaque forming units, 10 immunologically positive clones were obtained. These clones were plaque purified and the lysates of the purified clones were tested for the functional activity of TFI. The isopropyl-thiogalactoside induced phage lysates were absorbed on the nitrocellulose paper and screened for the $^{125}$I-Factor $X_a$ binding activity. FIG. 1 demonstrates that some of these immunologically positive clones showed the ability to bind the $^{125}$I-Factor $X_a$ on the nitrocellulose paper. In all, 3 out of 15 immunologically positive fetal liver clones, and 4 out of 10 immunologically positive placental clones showed $^{125}$I-Factor $X_a$ binding activity. These immunologically and functionally positive clones were digested with EcoR1 and the size of the inserts were estimated by gel electrophoresis. One clone from placental library (λP9) had an insert of approximately 1.4 kb, while all the other clones contain inserts of approximately 1.0 kb. Partial DNA sequencing has shown that 1.0 kb clones contain sequences identical to part of the longer 1.4 kb placental clone (λP9). The λP9 was therefore selected for complete sequencing.

Nucleotide sequence and predicted protein sequence of TFI cDNA isolate

The λP9 clone was subjected to restriction mapping, M13 subcloning and sequencing by the strategy shown in FIG. 2. The entire sequence was determined on both strands by the exonuclease III deletion method [Henikoff, *Gene* 28, 351–359 (1984)] and found to consist of 1432 bases in length. The sequence is shown in FIG. 3. It contains a 5′-noncoding region of 133 bases, an open reading frame of 912 nucleotides, and a 3′-noncoding region of 387 nucleotides. The first ATG occurs at nucleotide 134 in the sequence TAGATGA which was closely followed by a second ATG at nucleotide 146 in the sequence ACAATGA. These are possibly the initiation sequences, although they differ from the proposed consensus sequence for initiation by eukaryotic ribosome, ACCATGG [Kozak, *Cell* 44, 283–292 (1986)]. Twenty-eight amino acids precede a sequence corresponding to the N-terminal of the mature protein. The length and composition of the hydrophobic segment of these 28 amino acids are typical of signal sequences [Von Heijne, *Eur. J. Biochem.* 133, 17–21 (1983); *J. Mol. Biol.* 184, 99–105 (1985)]. A signal peptidase possibly cleaves at $Ala_{28}$–$Asp_{29}$ to give rise to a mature protein. The sequence predicted for mature TFI consists of 276 amino acids that contains 18 cysteine residues and 7 methionines. The calculated mass of 31,950 Daltons based on the deduced protein sequence for mature TFI is somewhat lower than the 37–40 kDa estimated by sodium dodecyl sulfate polyacrylamide gel electrophoresis of isolated protein, and the difference probably reflects the contribution of glycosylation to the mobility of the natural protein. The deduced protein sequence corresponding to the mature protein contains 3 potential N-linked glycosylation sites with the sequence Asn-X-Thr/Ser (amino acid positions 145, 195, and 256). Amino acid sequence analysis of purified whole TFI and two isolated proteolytic fragments match exactly the protein sequence deduced from cDNA sequence (FIG. 3, underlined), indicating the isolated cDNA clone encodes TFI. The 3'-noncoding region is A+T rich (70% A+T). Neither consensus polyadenylation signal, AATAAA [Proudfoot and Brownlee, *Nature* 252, 359–362 (1981)] nor the poly A tail was found in this clone, possibly due to artefactual loss of part of 3' terminal portion during construction of the library.

Charge distribution, hydrophobicity/hydrophilicity, and internal homology

The translated amino acid sequence of the TFI contains 27 lysines, 17 arginines, 11 aspartic acids, and 25 glutamic acids. The charge distribution along the protein is highly uneven as shown in FIG. 4. The signal peptide region contains 2 positively charged lysine with 26 neutral residues. The amino-terminal region of the mature protein contains a highly negatively charged stretch. Six of the first 7 residues are either aspartic acid or glutamic acid which are followed closely by two more negatively charged amino acids downstream before a positively charged lysine residue appears. The center portion of the molecule is generally negatively charged. At the carboxy terminal, there is a highly positively charged segment. The amino acids 265 to 293 of TFI contain 14 positively charged amino acids including a 6-consecutive arginine +lysine residues.

The predicted hydrophilicity/hydrophobicity profile of TFI protein is shown in FIG. 5. The signal peptide contains a highly hydrophobic region as expected. The rest of the molecule appears rather hydrophilic.

The translated amino acid sequence of TFI contains several discernible domains. Besides the highly negatively charged N-terminal domain and the highly positively charged C-terminal domain, the center portion consists of 3 homologous domains which have the typical sequences of the Kunitz-type inhibitors (see below).

Homology to other proteins

By searching the National Biomedical Research Foundation sequence data base, it was found that the N-terminal domain and C-terminal domain of TFI do not show significant homology to other known proteins. The 3 internal homologous domains, however, are each homologous to the sequences of other basic protease inhibitors including bovine pancreatic basic protease inhibitor (aprotinin), venom basic protease inhibitors, and inter-α-trypsin inhibitors (FIG. 6). It is noteworthy that disulfide bonding structure is highly conserved in all these inhibitors. Based on these homologies, it is clear that TFI belongs to the basic protease inhibitor gene superfamily.

Northern blotting

Poly(A)+ RNAs were purified from TFIproducing liver-derived cell lines, Chang liver, HepG2 hepatoma, and SK-HEP-1 hepatoma cells. The poly (A)+ RNAs were resolved by denaturing agarose gel electrophoresis, transblotted onto a nitrocellulose paper and probed with $^{32}$P-labeled TFI cDNA (λP9). As shown in FIG. 7, two major bands of hybridization were observed that corresponded to mRNAs of 1.4 kb and 4.4 kb in all three cell lines tested. Several other cell lines were tested which do not produce detectable amounts of TFI and in which no hybridization with the probe was found. (data not shown).

Various other examples will be apparent to the person skilled in the art after reading the present disclosure without departing from the spirit and scope of the invention. It is intended that all such further examples be included within the scope of the appended claims.

What is claimed is:

1. Human tissue factor inhibitor clone lambdaP9 containing a 1432 basepair insert as shown in FIG. 3 and characterized by the restriction enzyme cleavage map of FIG. 2.

2. The cDNA sequence having the nucleotide sequence shown in FIG. 3 which encodes human tissue factor inhibitor having the amino acid sequence shown in FIG. 3.

3. A cDNA sequence consisting of a nucleotide sequence encoding human tissue factor inhibitor which has the amino acid sequence of FIG. 3.

* * * * *

UNITED STATES PATENT AND TRADEMARK OFFICE
CERTIFICATE OF CORRECTION

PATENT NO. : 4,966,852
DATED : October 30, 1990
INVENTOR(S) : Tze-Chein Wun, Juniko K. Kretzmer and George J. Broze, Jr.

It is certified that error appears in the above-indentified patent and that said Letters Patent is hereby corrected as shown below:

In the drawings, in the amino acid sequence of Fig. 3, residue 76 should read --Thr--.

Signed and Sealed this

Thirteenth Day of December, 1994

Attest:

BRUCE LEHMAN

*Attesting Officer*   *Commissioner of Patents and Trademarks*